US006716248B2

United States Patent
Huene

(10) Patent No.: US 6,716,248 B2
(45) Date of Patent: Apr. 6, 2004

(54) CONFIGURABLE PROSTHETIC JOINT

(76) Inventor: Donald R. Huene, 201 N. Valeria, Fresno, CA (US) 93701

( * ) Notice: Subject to any disclaimer, the term of this patent is extended or adjusted under 35 U.S.C. 154(b) by 0 days.

(21) Appl. No.: 10/057,892

(22) Filed: Jan. 29, 2002

(65) Prior Publication Data

US 2003/0144739 A1 Jul. 31, 2003

(51) Int. Cl.$^7$ .................................................. A61F 2/38
(52) U.S. Cl. ................ 623/20.12; 623/20.11; 623/20.13; 623/20.15
(58) Field of Search ............... 623/20.11, 20.12, 623/20.13, 20.15, 57, 59, 18.11

(56) References Cited

U.S. PATENT DOCUMENTS

| | | | | |
|---|---|---|---|---|
| 3,708,805 A | * | 1/1973 | Scales et al. ................. 3/1 |
| 4,776,851 A | * | 10/1988 | Bruchman et al. ............ 623/13 |
| 5,314,484 A | * | 5/1994 | Huene .......................... 623/20 |
| 5,376,121 A | * | 12/1994 | Huene et al. ................. 623/20 |
| 5,443,465 A | * | 8/1995 | Pennig ......................... 606/59 |
| 5,879,390 A | * | 3/1999 | Kubein-Meesenburg et al. 623/20 |
| 6,027,534 A | | 2/2000 | Wack et al. .................. 623/20 |
| 6,290,725 B1 | * | 9/2001 | Weiss et al. ............. 623/20.12 |

FOREIGN PATENT DOCUMENTS

EP 1016386 A2 * 5/2000 ............. A61F/2/38

* cited by examiner

Primary Examiner—Bruce Snow
Assistant Examiner—Cheryl Miller
(74) Attorney, Agent, or Firm—Liniak, Berenato & White, LLC

(57) ABSTRACT

A prosthetic joint is disclosed that includes a plurality of elements, which may be provided in kit form, that can be assembled to form either a single-axis joint or a double-axis joint depending on whether an adaptor is used to join first and second elements of the joint.

16 Claims, 4 Drawing Sheets

CONFIGURABLE PROSTHETIC JOINT

FIELD OF THE INVENTION

The present invention is directed toward a prosthetic joint, and more specifically, toward a prosthetic joint that can be configured as either a single- or double-axis joint.

BACKGROUND OF THE INVENTION

The joints of a human body are subject to substantial stresses, and as people age, their joints often function less effectively than when they were younger. Injury and disease can also affect joint function. It is becoming increasingly common to replace natural joints in the human body with artificial ones when the natural joints wear out or no longer function properly. Artificial hips and knees are widely used, and other joints such as the elbow are also replaced on occasion.

Most artificial joints include a stem or anchor portion that is inserted into the bone on either side of the damaged joint and a pair of bearing surfaces at the protruding ends of the stems that interact with one another to form a joint. Various joints in the body are generally replaced with structurally similar artificial joints; thus a knee joint will generally be replaced with a hinge joint and a hip joint will be replaced with a ball-and-socket joint. In some cases, however, such as with elbow joints, it may be desirable to replace the natural joint with an artificial joint structurally different from the original joint to improve the function of the patient's joint. Thus a natural single-axis elbow joint is sometimes replaced with a prosthetic device that includes two pivotal axes. In this case, a stem embedded in an ulna connects to a central joint element at a first location and a stem embedded in a humerus connects to the central joint element at a second location spaced apart from the first location so that both posts pivot about different, normally parallel, axes. Such bi-axial elbow joints and the benefits and uses thereof are described in greater detail in U.S. Pat. Nos. 5,314,484 and 5,376,121 which patents are hereby incorporated by reference.

The type of replacement joint selected by a surgeon will depend on many factors including the age, health and activity level of the patient and the size and condition of the bones adjacent the joint being replaced. Unfortunately, it is often difficult to determine which of these joint types should be used until a patient's joint has been exposed during surgery. This is especially true in elbow replacement surgery where a the need for a double axis joint is often not evident until the damaged joint can be directly examined. Thus, a surgeon may need to obtain both types of joints prior to a surgery even though only one joint will be used. Because double-axis elbows are used less frequently that single-axis joints, and are also more expensive than single-axis joints, surgeons may tend to use a single-axis joint even in cases where a double-axis joint would be more appropriate. Moreover, because a surgeon may need to partially install or modify one of the artificial joints before determining that a different device would be preferable, it may be necessary to discard one of the two prostheses at a considerable cost.

It is known to provide certain types of prosthetic joints in kit form which kits include a plurality of different elements, some or all of which may be used to form a given joint depending on the condition of the natural joint as revealed by surgery. For example, U.S. Pat. No. 6,027,534 describes a modular elbow kit that includes three different bearing elements. A first element is used when the elbow joint is to be configured in a constrained mode and a second and third element are used instead of the first element when the joint is to function in an unconstrained mode. Beneficially, the same kit can be used in a wide variety of patients. Stocking identical kits is generally less expensive that stocking a variety of different prosthetics, and, as a majority of the items in each kit will be used in every surgery, waste is minimized.

It would be therefore be desirable to provide a kit for forming a prosthetic joint that could be assembled to produce either a single-axis joint or a double-axis joint.

SUMMARY OF THE INVENTION

This problem is overcome by the present invention which comprises a prosthetic joint configurable as either a single-axis joint or a double-axis joint. While the subject invention could be used in various parts of the body, it finds particular utility as an elbow joint, and hereinafter, the invention will primarily be described in terms of an elbow joint, it being understood that it could also function in other locations in the body such as the knee.

In general terms, the invention comprises the provision of an adaptor for use with a single-axis joint to convert the single-axis joint to a double-axis joint when called for. The adaptor may be sold by itself or as part of a kit with the single-axis joint. An ordinary single-axis joint includes a first element insertable in a first bone, such as a humerus and a second element insertable into a second bone such as an ulna. The distal end of the humeral component and the proximal end of the ulnar component extend from the respective bones, and the distal end of the humeral element has a first shape and the proximal of the second element has a second shape complimentary to the first shape. By complimentary, it is meant that the first shape mates or fits with the second shape to form a joint. Thus a sphere and a depression would be complementary shapes (mating like a ball-and-socket joint) as would a single arm receivable between a pair of spaced-apart arms (a hinge joint). The typical joint also includes a pin or similar connector for pivotably joining the distal end of the humeral element to the proximal end of the ulnar component. To convert the single-axis joint to a double axis joint, a connector or adaptor is provided that has a first end having a shape complementary to the shape of the distal end of the humeral component and a second end having a shape complementary to the shape of the ulnar component which adaptor can thus be placed between the ends of the humeral and ulnar components and pivotally connected to each to form a double axis joint. In the preferred embodiment, the complementary shapes are described as a first end of a first element that is received between the spaced apart arms of a second element; however other complementary shapes could be used as well.

In a preferred embodiment, the invention comprises a humeral component having a stem portion for insertion into the interior of a humerus and a second end, an ulnar component having a first end for insertion into the interior of an ulna and a second end, and a connector for pivotably joining the second ends to form a joint. A first connector comprises a pin that directly connects the second ends of the components to form a single-axis joint while a second, alternate, connector comprises a spacing element that has a first portion connectable to the second end of the humeral element with a pin and a second portion connectable to the second end of the ulnar element with a pin to form a double-axis joint. The first portion of the spacing element is generally similar in shape to the second end of the ulnar element while the second portion of the spacing element is generally similar in shape to the second end of the humeral element.

The second end of the humeral element includes a pair of parallel, spaced apart arms each having a bore which bores are coaxially aligned. The second end of the ulnar element is somewhat narrower than the spacing between the arms of the humeral element and includes a bore of approximately the same diameter as the bores in the humeral element arms so that when the bore in the ulnar element is aligned with the bores in the humeral element and a pin is inserted through the aligned bore, a joint is formed. A bearing insert is also preferably used between the ulnar and humeral elements to reduce wear and keep the ulnar element properly spaced with respect to the humeral element.

The connector of the preferred embodiment is generally Y-shaped and includes two parallel arms that extend from a body portion in a first direction and a third arm that is centered between and parallel to the first and second arms but which extends from the body portion in a direction opposite to the first and second arms. To form a double-axis joint, the third arm of the connector is connected between the arms of the humeral element with a pin and the second end of the ulnar element is connected between the parallel arms of the connector with a pin to form a double-axis joint. The prosthesis is sold in kit form so that a surgeon need obtain only one kit, and the surgeon can install the joint with or without the connector depending on the condition of the natural joint as revealed by surgery.

It is therefore a primary object of the present invention to provide an artificial joint configurable as either a single-axis joint or a double-axis joint.

It is another object of the invention to provide a method of installing an artificial joint as either a single-axis joint or a double-axis joint.

It is a further object of the invention to provide an adaptor for converting a single-axis joint to a double axis joint.

It is still another object of the invention to provide a kit for assembling a prosthetic joint.

It is still a further object of the invention to provide a prosthetic joint kit that includes a first element for connection to a first bone, a second element for connection to a second bone, and two connectors, either of which can be used to pivotably connect the first and second elements.

In furtherance of the foregoing objects, a prosthetic elbow is disclosed that includes a humeral component and an ulnar component adapted to pivotably engage the humeral component and an adaptor having a first end pivotably connected to the ulnar component and a second end pivotably connected to the humeral component.

Also disclosed is a kit assembleable in a first configuration to form a single-axis prosthetic joint and in a second configuration to form a double-axis prosthetic joint that includes a first component having a proximal end insertable into a first bone and a distal end, a second component having a distal end insertable into a second bone and a proximal end, and an adaptor connectable between the first component and the second component. The kit is assembled by connecting the first component directly to the second component to form a single-axis joint or by connecting the adaptor between the first component and the second component to form a double-axis joint.

A method of assembling a prosthetic joint is also disclosed that includes the steps of providing a first joint component having a first end adapted to be inserted into the interior of a first bone and a second end, a second joint component having a first end adapted to be inserted into the interior of a second bone and a second end, a first connector for forming a single-axis pivotal connection between the first component and the second component, and a second connector for forming a double-axis pivotal connection between the first component and the second component. Then one of the first and second connectors is selected and used to connect the first component to the second component.

A double-axis prosthetic joint is also described that is formed from a first component having a proximal end adapted to be mounted in a first bone and a distal end comprising a pair of spaced apart arms and a second component having a distal end adapted to be mounted in a second bone and a proximal end including a bore. The joint also includes a connector for pivotably connecting the first component to the second component which connector has a first end having a bore which is pivotably mounted between the first component spaced apart arms and a second end comprising a pair of spaced apart arms. The second component distal end is pivotably mounted between the connector second end spaced apart arms.

Another aspect of the invention comprises a prosthetic joint kit including a first component having a first end and a second end comprising a pair of spaced apart arms and a second component having a first end and a second end comprising a bore. The kit also includes a first connector for pivotably connecting the first component directly to the second component and a second connector for pivotably connecting the first component indirectly to the second component.

Another aspect of the invention comprises a method of converting a single-axis prosthetic joint to a double-axis prosthetic joint that includes the steps of providing a first joint element having a first end insertable into a bone and a second end having a first shape, and a second joint element having a first end insertable into a bone and a second end having a second shape complementary to the first shape. The second end is pivotably connectable to the first joint second end to form a single-axis prosthetic joint. A connector is also provided that has a first end having a shape complementary to the first shape and a second end complementary to the second shape that can be used to pivotally attach the first joint element second end to the connector first end, and the second joint element second end to the connector second end to form a double-axis prosthetic joint.

BRIEF DESCRIPTION OF THE DRAWINGS

These and other objects and aspects of the invention will be better understood from a reading of the detailed description of the invention provided below together with the following drawings.

DETAILED DESCRIPTION OF THE INVENTION

Figure 1:
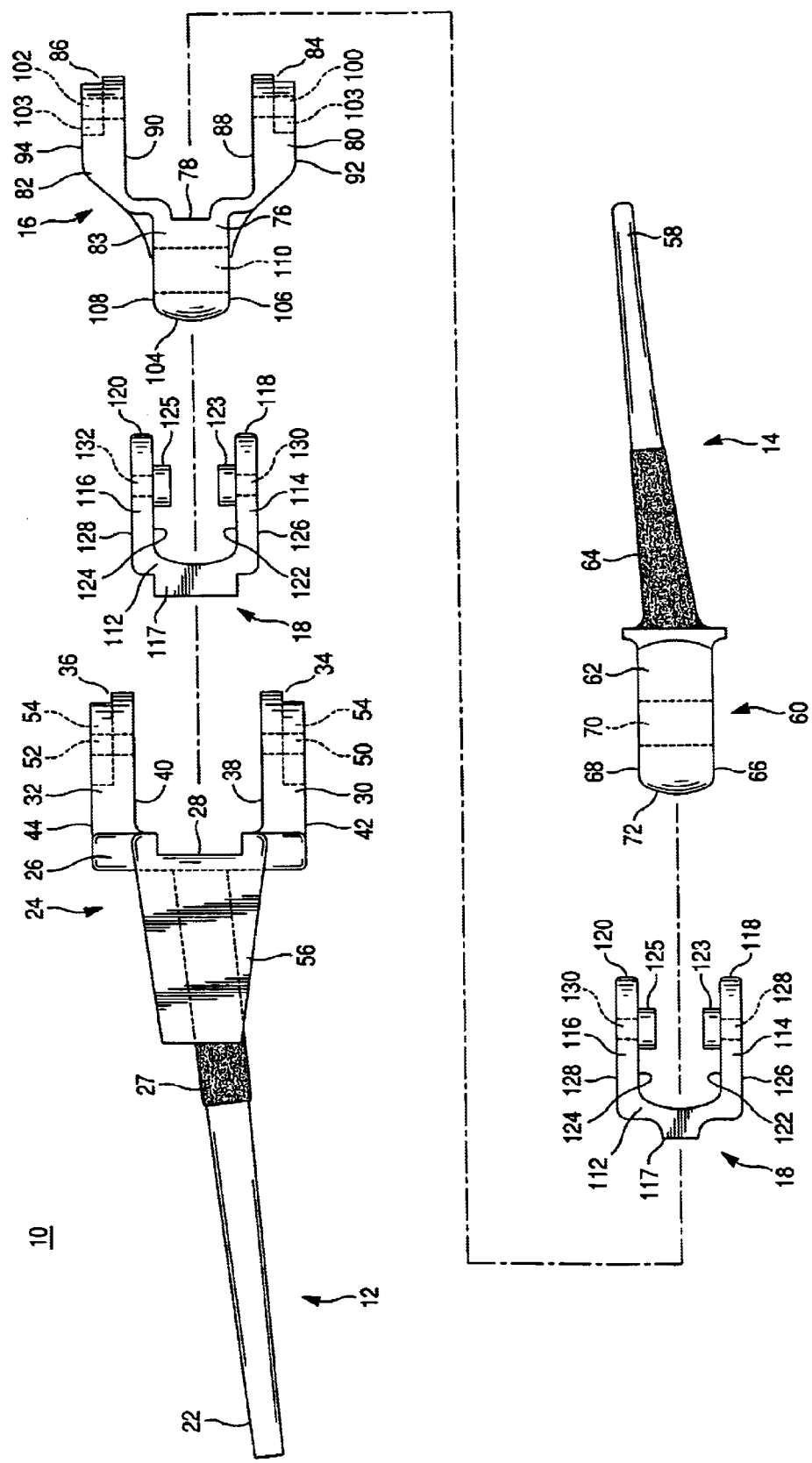
FIG. 1 is an exploded top plan view of an artificial joint according to the present invention.
Figure 2:
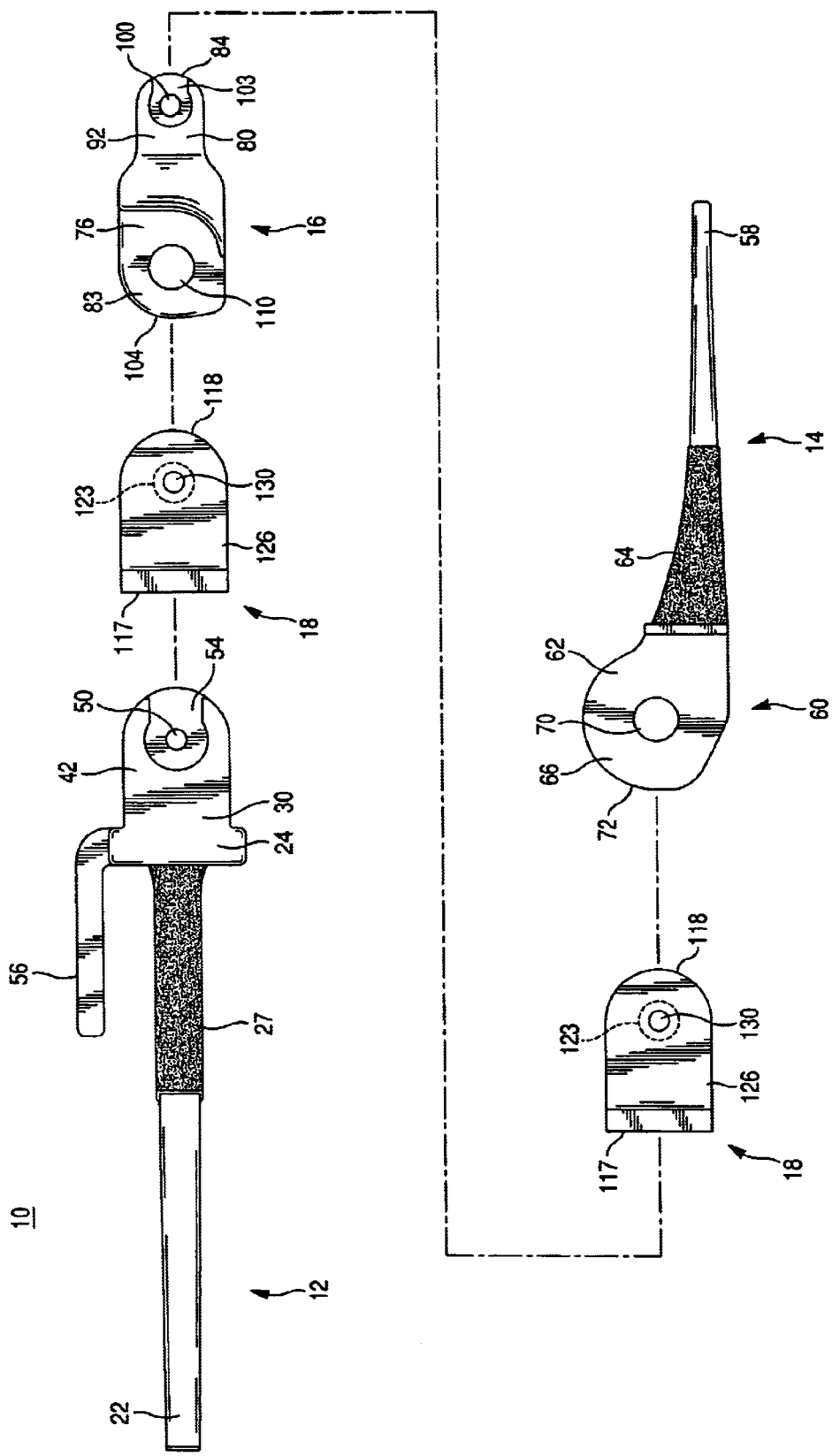
FIG. 2 is an exploded side elevational view of the artificial joint of FIG. 1.

Referring now to the drawings, wherein the showings are for the purpose of illustrating a preferred embodiment of the invention only and not for the purpose of limiting same, FIGS. 1 and 2 shows the elements of an artificial joint 10 according to the present invention, namely, a first or humeral component 12, a second or ulnar component 14, an adaptor or connector 16 and two bearing inserts 18. The preferred embodiment of the invention comprises an artificial elbow joint, and therefore, various components are described as being connectable to a humerus in a person's upper arm and an ulna in a persons forearm. The terms "proximal" and "distal" are used herein relative to the portion of the human body in which the joint will be installed, even though a body it not shown in the figures. Thus, for example, the proximal end of the humeral component is the end that will be inserted into a humerus when the joint is in place in a body and the distal end of the humeral component will extend from the humerus.

All components described below, with the exception of inserts 18 are formed from a surgical grade metal, steel or titanium or alloys thereof, for example, while inserts 18 are formed from a standard implant-grade high molecular weight polyethylene.

Humeral component 12 includes a proximal end 22, a distal end 24 and a head 26. A portion 27 of distal end 24 is roughened or coated with a granular material to provide a larger surface area for bone to attach to as it grows around the stem. Head 26 includes a first wall 28 from which extends a first arm 30 and a second arm 32 parallel to the first arm and spaced apart therefrom by a first distance. Arms 30 and 32 have ends 34 and 36, inner walls 38 and 40, and outer walls 42 and outer wall 44, respectively. First arm 30 includes a bore 50 extending between inner wall 38 and 42 while second arm 32 includes a bore 52 coaxially aligned with bore 50 and extending between inner wall 40 and outer wall 44. Outer walls 42 and 44 each include U-shaped notches 54 extending inwardly from ends 34 and 36. A stop plate 56 is also provided on the distal end of the humeral component for limiting the angular movement of the assembled joint.

Ulnar component 14 includes a distal end 58 and a proximal end 60 having a head 62 and a portion 64 roughened or coated with a granular material to provide a larger surface area for connection to an ulna. Head 62 includes parallel sidewalls 66, 68 connected by a bore 70 and a rounded end wall 72.

Adaptor or connector 16 includes a body portion 76 having a first wall 78 from which a first arm 80 and a second arm 82 extend and a third arm 83 that extends from the opposite side of the body portion from the first and second arms. Arms 80 and 82 have ends 84 and 86, inner walls 88 and 90, and outer walls 92 and 94, respectively. First arm 80 includes a bore 100 extending between inner walls 88 and outer wall 92 while second arm 82 includes a bore 102 coaxially aligned with bore 100 and extending between inner wall 90 and outer wall 94. Outer walls 92 and 94 include U-shaped notches 103 surrounding the opening of bores 100 and 102. Third arm 83 includes a rounded end wall 104 and first and second parallel sidewalls 106, 108 and a bore 110 extending between the first and second sidewalls.

Bearing inserts 18 are generally U-shaped and include a body portion 112, first and second arms 114, 116 extending from the body portion, and a projection 117 extending from the opposite side of body portion 112. Arms 114, 116 include ends 118, 120, inner walls 122, 124 having inwardly facing bosses 123, 125, and outer walls 126, 128 respectively. The bosses 123, 125 have outer widths sized to fit within bores 70 and 110 of the connector and the ulnar component in a manner that allows the connector and the ulnar component to be pivotably supported by the bosses. First arm 114 includes a bore 130 that extends through the first arm and boss 123 and second arm 116 includes a bore 132 coaxially aligned with first bore 130 that extends through the second arm 116 and the second boss 125.

Figure 3:
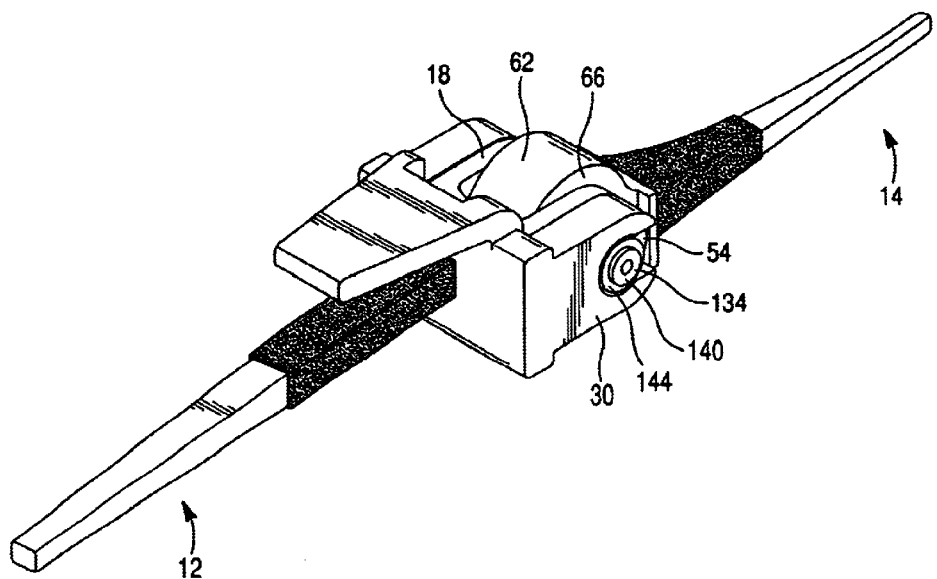
FIG. 3 is a perspective view of an artificial joint according to the present invention configured as a single-axis joint.
Figure 4:
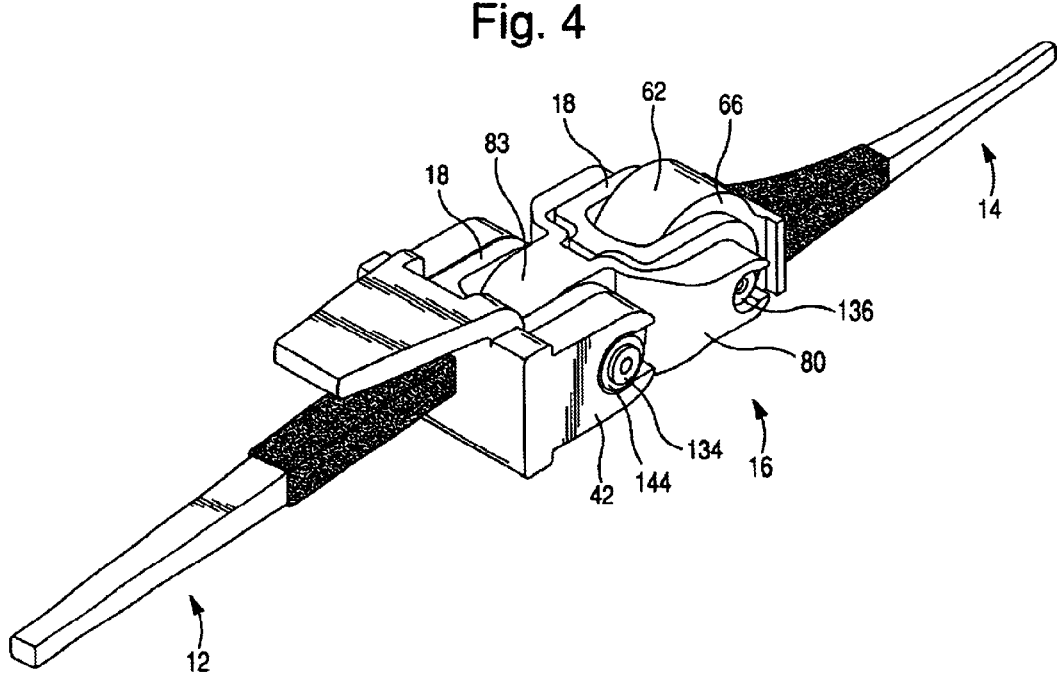
FIG. 4 is a perspective view of an artificial joint according to the present invention configured as a double axis joint.
Figure 5:
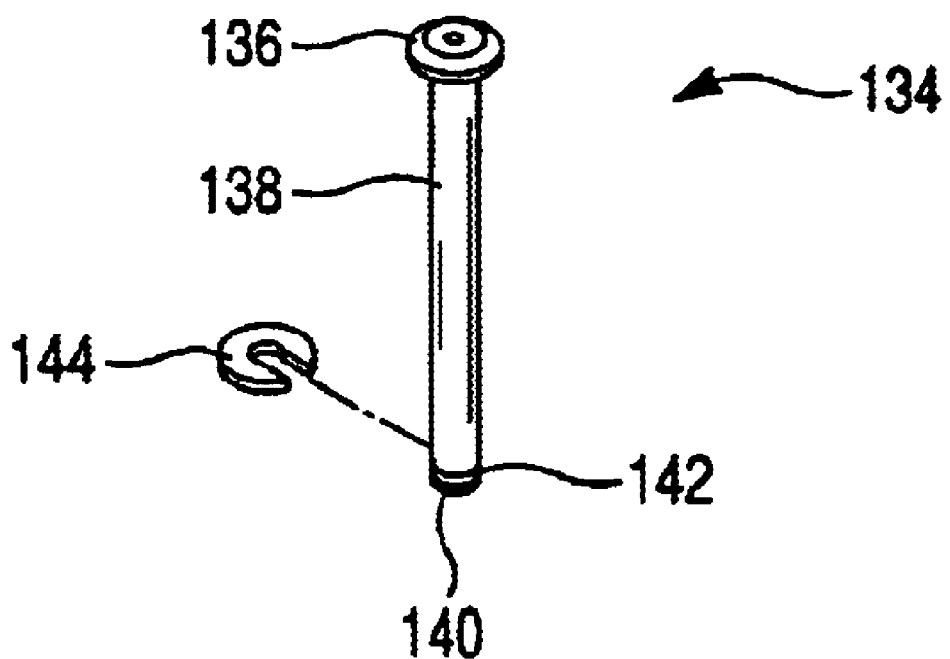
FIG. 5 is a perspective view of a pin and clip for connecting the elements of the subject artificial joint.

The parts described above can be assembled in one of two ways to form either a single-axis joint as shown in FIG. 3 or a double-axis joint as shown in FIG. 4. Preferably, all elements are sold together in kit form so that a surgeon performing a joint replacement will have all the necessary pieces for forming the type of joint dictated by the condition of the patient's natural joint. Pins 134, one of which is shown in FIG. 5, are provided for pivotably connecting the various elements of the kit which pins include a first end 136, a cylindrical body 138, and a second end 140 with an annular groove 142 spaced inwardly from end 140. A clip 144 engages annular groove 142 to secure the pin as will be described below.

When it is determined that a single-axis joint is needed, the artificial joint is assembled as follows: the arms 114, 116 of bearing insert 18 are spread so that head 62 of ulnar portion 14 can be inserted between bosses 123, 125. The insert is then allowed to return to its unflexed shape with bosses 123, 125 projecting into bore 70. Insert 18 is next inserted into the gap between first and second arms 30, 32 of humeral portion 12 with projection 117 of the insert abutting first wall 28 of the humeral portion and with outer wall 126 of first bearing insert first leg 114 adjacent inner wall 38 of the first leg of the humeral portion and outer wall 128 of the first bearing insert second arm 116 adjacent inner wall 40 of the second leg of the humeral portion with bores 130, 132 of the bearing insert aligned with humeral portion first leg bore 50 and humeral portion second leg bore 52. A pin 134 is the inserted through the aligned bores until first end 136 enters the U-shaped notch 54 on the side of first arm 30 and the second end 140 extends from bore 52 in second arm 32. A clip 144 having a diameter greater than the width of U-shaped notch 54 in arm 32 is then snapped around annular groove 142 to prevent pin 134 from being withdrawn through the bores in the annular element. The humeral and ulnar components of the joint are then installed in a humerus and an ulna in the standard manner.

When it is determined that a double-axis joint is needed, connector 16 and a second bearing insert 18 are installed between the humeral element 12 and the ulnar element 14. The arms 114, 116 of a first bearing insert 18 are spread so that third arm 83 of adaptor 16 can be inserted therebetween and the insert is then released to allow bosses 123, 125 to project into bore 110 of the adaptor. The adaptor and insert are then placed between the first and second arms 30, 32 of the humeral element with bores 50, 52 of the humeral component aligned with the adaptor bore 110 and attached with a pin 134 as described above. A second bearing insert 18 is then attached to head 62 of ulnar element 14 by spreading the arms of the insert and placing the bosses 125, 123 of the insert into bore 70 of ulnar element 14. The bearing element mounted to head 62 of ulnar element 14 is next placed into the gap between arms 80, 82 of adaptor 16 with bore 70 of the ulnar element aligned with the bores 100, 102 in the adaptor arms 80, 82, and the adaptor is fastened to the ulnar element using a pin as described above. The joint thus formed has a first pivotal axis at the first pin connecting the humeral element to the connector and a second pivotal axis at the second pin that connects the ulnar element to the second end of the connector.

The invention has been described in terms of a preferred embodiment, it being understood that numerous obvious modifications and additions to this embodiment will become apparent to those skilled in the relevant arts upon a reading and understanding of this description. It is intended that all such modifications and additions be a part of the subject invention to the extent that they are included within the scope of the several claims appended hereto.

I claim:

1. A kit assembleable in a first configuration to form a single-axis prosthetic elbow joint or in a second configuration to form a double-axis prosthetic elbow joint comprising:
   a first component having a proximal end insertable into a first bone and a distal end having a first arm and a second arm spaced apart by a first distance;
   a second component having a distal end insertable into a second bone and a proximal end pivotably securable to the distal end of said first component to form a single-axis joint, said second component proximal end having a width less than said first distance and a bore; and
   an adaptor having a first end pivotably securable to the distal end of said first component and a second end pivotably securable to the proximal end of said second component to form a double-axis joint, said adaptor first end having a width less than said first distance and said adapter second end comprising first and second arms spaced apart by said first distance, wherein said prosthetic elbow joint is fully implantable within a body.

2. The kit of claim 1 including a U-shaped spacer mounted between said first component first arm and said first component second arm and having first and second legs having inner and outer sides, wherein the distance between said outer sides is approximately equal to said first distance and wherein the spacing between said inner sides is approximately equal to the width of said second component proximal end.

3. The kit of claim 2, wherein said spacer is formed from an implant grade high molecular weight polyethylene.

4. The kit of claim 1 including a U-shaped spacer mounted between said adaptor first arm and said adaptor second arm and having first and second legs having inner and outer sides, wherein the distance between said outer sides is approximately equal to said first distance and wherein the spacing between said inner sides is approximately equal to the width of said adaptor first end.

5. The kit of claim 4, wherein said spacer is formed from an implant grade high molecular weight polyethylene.

6. The kit of claim 1 including a pin connecting said first component proximal end to the first end of said adaptor.

7. The kit of claim 1 including a pin connecting said second component proximal end to the second end of said adaptor.

8. The kit of claim 1, wherein each of said first and second arms of said first component distal end has a bore having a first diameter.

9. The kit of claim 8, wherein said first arm bore and said second arm bore are coaxially aligned.

10. The kit of claim 8, wherein said bore of said second component proximal end has a diameter approximately equal to said first diameter.

11. The kit of claim 1, wherein said first and second components and said adapter are formed from a material selected from a surgical grade metal.

12. The kit of claim 11, wherein said first and second components and said adapter are formed from a metal selected from the group consisting of steel, titanium, and alloys thereof.

13. The kit of claim 1, wherein a portion of said first component proximal end is roughened.

14. The kit of claim 1, wherein a portion of said second component distal end is roughened.

15. A method of assembling a prosthetic elbow joint comprising the steps of:
   providing a first joint component having a first end and a second end, the first end adapted to be inserted into the interior of a first bone;
   providing a second joint component having a first end and a second end, the first end adapted to be inserted into the interior of a second bone and the second end pivotably securable to the second end of the first joint component for forming a single-axis pivotal connection between the first joint component and the second joint component;
   providing a connector having a first end pivotably connectable to the second end of the first joint component and a second end pivotably connectable to the second end of the second joint component for forming a double-axis pivotal connection between the first joint component and the second joint component;
   selecting one of the single-axis pivotal connection and the double-axis pivotal connection; and
   connecting the second end of the first joint component to one of the second joint component for the single-axis pivotal connection, and the connector pivotably connected to the second joint component for the double-axis pivotal connection, wherein the prosthetic elbow joint is fully implantable within a body.

16. A method of converting a single-axis prosthetic elbow joint to a double-axis prosthetic elbow joint fully implantable within a body comprising the steps of:
   providing a first joint element having a first end insertable into a bone and second end having a first shape;
   providing a second joint element having a first end insertable into a bone and a second end having a second shape complementary to said first shape, said second end being pivotably securable to said first joint second end to form a single-axis prosthetic joint;
   providing a connector having a first end having a shape complementary to said first shape and a second end complementary to said second shape;
   pivotably attaching said first joint element second end to said connector first end; and
   pivotably attaching said second joint element second end to said connector second end to form a double-axis prosthetic joint.

* * * * *